US011999923B2

(12) United States Patent
Zha et al.

(10) Patent No.: US 11,999,923 B2
(45) Date of Patent: Jun. 4, 2024

(54) PROCESS FOR ENZYMATIC OIL DEGUMMING

(71) Applicant: DSM IP ASSETS B.V., Heerlen (NL)

(72) Inventors: Ying Zha, Echt (NL); Arjen Sein, Echt (NL); Willem Bijleveld, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 815 days.

(21) Appl. No.: 17/052,907

(22) PCT Filed: May 6, 2019

(86) PCT No.: PCT/EP2019/061538
§ 371 (c)(1),
(2) Date: Nov. 4, 2020

(87) PCT Pub. No.: WO2019/215078
PCT Pub. Date: Nov. 14, 2019

(65) Prior Publication Data
US 2021/0371770 A1 Dec. 2, 2021

(30) Foreign Application Priority Data
May 7, 2018 (EP) .................... 18171015

(51) Int. Cl.
*C11B 3/00* (2006.01)
(52) U.S. Cl.
CPC ...... *C11B 3/003* (2013.01); *C12Y 301/01032* (2013.01)

(58) Field of Classification Search
CPC . C11B 3/003; C11B 1/025; C12Y 301/01032; C12N 9/20
See application file for complete search history.

(56) References Cited

U.S. PATENT DOCUMENTS

2016/0289658 A1* 10/2016 Borch .................. C12Y 301/01

FOREIGN PATENT DOCUMENTS

| EP | 0575133 A2 | 12/1993 |
| WO | 9705219 A1 | 2/1997 |
| WO | 9818912 A1 | 5/1998 |
| WO | 2011/051322 A1 | 5/2011 |
| WO | 2013121047 A1 | 8/2013 |

OTHER PUBLICATIONS

International Search Report Issued in Counterpart Application No. PCT/EP2019/061538, dated Aug. 16, 2019.
"Lipase [Aspergillus niger CBS 513.88]—Protein—NCBI", Genbank accession No. XP_001393532.1, Mar. 3, 2011, ncbi.nlm.nih.gov/protein/XP_001393532.1.

* cited by examiner

*Primary Examiner* — Deborah D Carr
(74) *Attorney, Agent, or Firm* — McBee Moore & Vanik IP, LLC

(57) ABSTRACT

The present invention relates to a process for reducing an amount of intact phospholipids in a triacylglyceride oil comprising incubating the oil with a polypeptide having phospholipase A1 activity, wherein the polypeptide comprises a polypeptide having at least 80% identity to the mature amino acid sequence of SEQ ID NO: 1.

17 Claims, 1 Drawing Sheet
Specification includes a Sequence Listing.

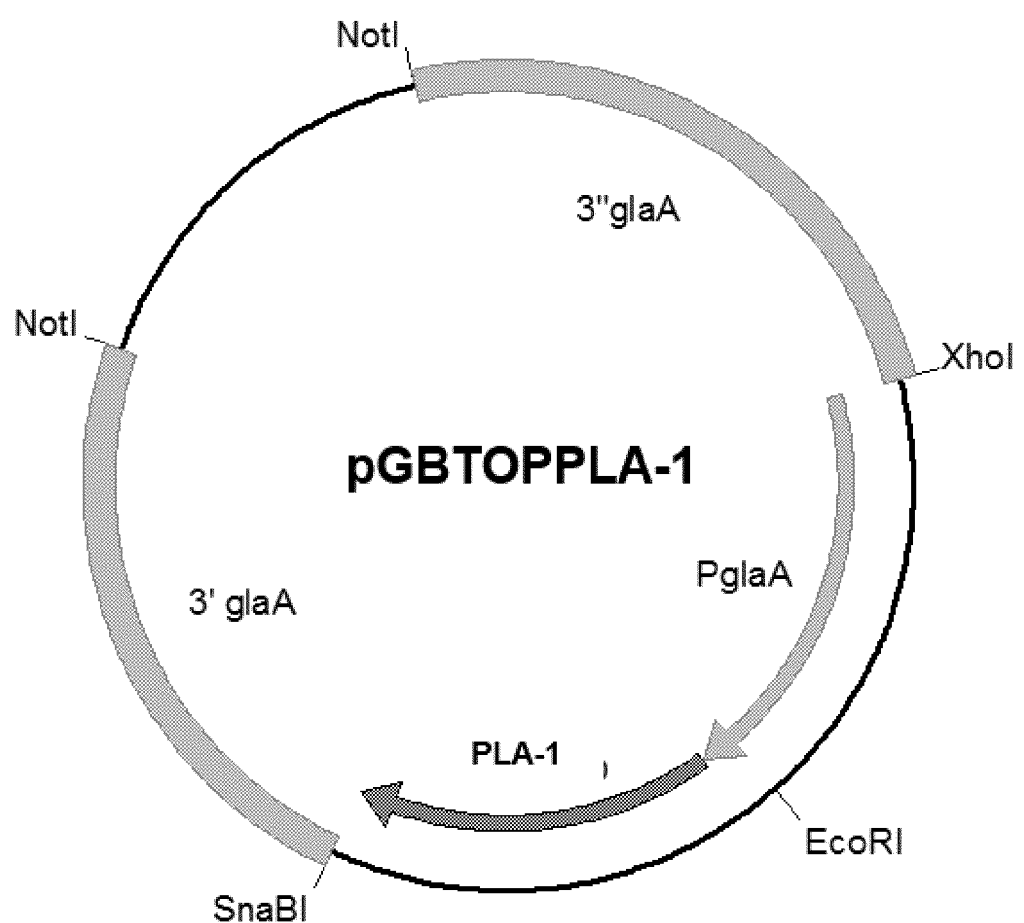

PROCESS FOR ENZYMATIC OIL DEGUMMING

CROSS-REFERENCE TO RELATED APPLICATIONS

This application is the National Stage entry of International Application No. PCT/EP2019/061538, filed 6 May 2019, which claims priority to European Patent Application No. 18171015.3, filed 7 May 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-542000_ST25.txt" created on 3 Nov. 2020, and 9,267 bytes in size) is submitted concurrently with the instant application, and the entire contents of the Sequence Listing are incorporated herein by reference.

BACKGROUND

Field

The present invention relates to a process for reducing an amount of phospholipids in a triacylglyceride oil using an enzyme having phospholipase A1 activity.

Description of Related Art

Crude vegetable oils obtained from either pressing or solvent extraction methods are a complex mixture of triacylglycerols, phospholipids, sterols, tocopherols, free fatty acids, trace metals, and other minor compounds. In soybean oil processing, the soy seed may first be flaked before hexane extraction to obtain a flake oil. In another commonly known process, the seed is first treated by an expander before extraction, resulting in an expander oil. The latter usually leads to higher oil yield, but also to a higher phospholipid content. During the preparation of other oils such as canola or rapeseed oil, seeds are first pressed leading to a pressed oil fraction. The press cake can be further treated with a solvent to yield an extracted oil fraction and the two fractions combined are known as crude oil for canola, rapeseed or sunflower.

It is desirable to remove the phospholipids, free fatty acids and trace metals in order to produce a high-quality edible oil. The most commonly used processes in industry are water or wet degumming, acid degumming, caustic refining and enzymatic degumming or refining. Generally, the removal of phospholipids generates the majority of the losses associated with the degumming of vegetable oils. Since most phospholipid molecules possess both a hydrophilic functional group and lipophilic moiety consisting of a glycerol with two fatty acid chains, they tend to be excellent natural emulsifiers. Therefore, it is desirable to hydrolyze phospholipids into their lyso- or phosphorous (glycerophphosphate)-forms and so reduce the emulsifying property. The major phospholipids in vegetable oils are phosphatidyl choline (PC), phosphatidyl ethanolamine (PE), phosphatidyl inositol (PI) and phosphatidic acid (PA).

Various processes are known for enzymatic degumming or enzymatic refining of vegetable oils, using enzymes with phospholipase activity, such as phospholipase A1, phospholipase A2, phospholipase C, or phosphatidyl inositol phospholipase C activity.

WO9705219 discloses a process for reducing the content of phosphorous containing components in vegetable oils using a phospholipase enzymes mixture from *Aspergillus niger*, comprising a phospholipase A2, and/or a phospholipase A1 activity and a lysophospholipase activity.

EP0575133 teaches a phospholipase A1 (PLA1) enzyme from an *Aspergillus oryzae* and an *Aspergillus niger* strain and the use of these phospholipases for preparing lysophospholipids from a phospholipid substrate for instance derived from animals, plants and microorganisms. EP0575133 discloses that the residual activity of the PLA1 from *A. niger* after a temperature treatment at 70° C. was only about thirty percent (30%) of the residual activity after a temperature treatment at 50° C. and 60° C. The PLA1 of *A. oryzae* did not exhibit any activity after a temperature treatment at 70° C. EP0575133 does not teach a process for enzymatic degumming of an edible oil.

US20160289658 discloses a phospholipase derived from *Talaromyces leycettanus*. This phospholipase showed a relatively high thermostability and showed a higher activity at 70° C. than the commercial enzyme preparation Lecitase Ultra.

WO2011/051322 discloses a phospholipase from *Aspergillus fumigatus*, which hydrolysed phospholipids in soy oil at a temperature of 55° C. and 60° C.

There is a need for an improved process for reducing the content of phospholipids in a tricacylglyceride oil using phospholipases that are active at a broad temperature range.

SUMMARY

The present invention relates to a process for reducing an amount of intact phospholipids in a triacylglyceride oil, comprising incubating the oil with a polypeptide having phospholipase A1 activity, wherein the phospholipase A1 comprises a polypeptide having at least 80% identity to the mature amino acid sequence of SEQ ID NO: 1. It was found that the phospholipase A1 which has at least 80% identity to the mature amino acid of SEQ ID NO: 1 was capable of reducing at least 85% of phospholipids originally present in a triacylglyceride oil at a broad temperature range of 55° C. to 70° C. within 4 hr. A phospholipase A1 in a process as disclosed herein is a phospholipase A1 which hydrolyses at least 85%, 86%, 87%, 88%, 89% or at least 90% of the amount of intact phospholipids originally present in a triacylglyceride oil when incubated with the oil in an amount of 0.28 mg active protein/kg oil at a temperature of between 55° C., 60° C., 65° C. and 70° C. for 4 hr.

Definitions

A "mature polypeptide" is defined herein as a polypeptide in its final form and is obtained after translation of a mRNA into polypeptide and post-translational modifications of said polypeptide. Post-translational modifications include N-terminal processing, C-terminal truncation, glycosylation, phosphorylation and removal of leader sequences such as signal peptides, propeptides and/or prepropeptides by cleavage.

A phospholipid is also indicated as a glycerophospholipid. A phospholipid as used herein is an "intact" phospholipid and comprises a glycerol backbone comprising two fatty acids and a phosphoric acid. A phospholipid is also indicated as diacylglyceride comprising a phosphate group.

A lysophospholipid is a glycerol backbone comprising only one acyl (fatty acid) group, and a phosphate group. A lysophospholipid can be formed after removal of an acyl group from phospholipids by the action of a phospholipase A1, and/or a phospholipase A2.

The wording triacylglyceride oil and triglyceride oil are used interchangeably herein. A triglyceride is an ester derived from glycerol and three fatty acids. A triacylglyceride oil can be an edible oil and/or an oil used as a biodiesel.

Sequence identity, or sequence homology are used interchangeable herein. In order to determine the percentage of sequence homology or sequence identity of two amino acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp. 276-277, emboss-.bioinformatics.nl). For protein sequences EBLOSUM62 is used for the substitution matrix. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The protein sequences disclosed herein can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

The terms "variant" can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

DETAILED DESCRIPTION

The present invention relates to a process for reducing an amount of intact phospholipids in a triacylglyceride oil comprising incubating the oil with a polypeptide having phospholipase A1 activity, wherein the polypeptide comprises a polypeptide having at least 80% identity to the mature amino acid sequence of SEQ ID NO: 1. A polypeptide having phospholipase activity which has at least 80% identity to the mature amino acid sequence of SEQ ID NO: 1 may be a polypeptide that is capable of reducing, or reduces at least 80%, 81%, 82%, 83%, 84%, 85%, 86%, 87%, 88%, 89% or at least 90% of the phospholipids originally present in the oil when the phospholipase A1 is incubated with the oil in an amount of 0.28 mg active protein/kg oil at a temperature of 55° C., 60° C., 65° C., and/or 70° C. for 4 hr, for instance in process as disclosed herein.

The polypeptide having phospholipase A1 activity in a process for reducing an amount of intact phospholipids in a triacylglyceride oil as disclosed herein may be a polypeptide that is capable of reducing, or reduces at least 80%, 81%, 82%, 83%, 84% or at least 85% of phospholipids originally present in the oil when the phospholipase A1 is incubated with the oil in an amount of 0.1-0.4, such as 0.2-0.3, or 0.28 mg active protein/kg oil at a temperature of 55° C., 60° C., 65° C., and/or 70° C. for 4 hr. The oil may further comprise 500 ppm citric acid and 3 wt % of water.

Surprisingly, it was found that a polypeptide having a phospholipase A1 activity in a process as disclosed herein was capable of reducing, or reduces at least 80%, 81%, 82%, 83%, 84%, 85%, 86%, 87%, 88%, 89%, or at least 90%, for instance from 85% to 99% such as from 86% to 98% such as from 87% to 97%, such as from 88% to 96%, such as between 89% and 95%, such as between 90%, and 94% of phospholipids originally present in an oil at a broad temperature range of between 55° C. and 70° C. A phospholipase A1 as disclosed herein may be incubated with the oil at a temperature range of from 55° C. to 70° C. during a period of 4 hr.

In one embodiment a process for reducing an amount of intact phospholipids as disclosed herein is a process wherein the amount of intact phospholipids that is reduced is at least 80%, 81%, 82%, 83%, 84%, 85%, 86%, 87%, 88%, 89%, or at least 90%, for instance from 85% to 99% such as from 86% to 98% such as from 87% to 97%, such as from 88 to 96%, such as from 89% to 95%, such as from 90% to 94% of the amount of intact phospholipids originally present in the oil. Surprisingly, it was found that the amount of intact phospholipids was reduced at a temperature of 55° C., 60°

C., 65° C., and/or at a temperature of 70° C. after incubating the oil with a phospholipase A1 in an amount of 0.1 to 0.4 mg active protein/kg oil, such as 0.28 mg active protein/kg oil after 4 hr incubation.

Phosphorous components such as phospholipids, lysophospholipids and phosphate esters can be determined using $^{31}$P-NMR and/or HPLC for instance as disclosed in the materials and methods section.

A polypeptide having phospholipase A1 activity as used herein is a phospholipase A1 according to enzyme classification E.C. 3.1.1.32. Phospholipase A1 is an enzyme that cleaves a phospholipid at the SN1 position forming a lysophospholipid and a fatty acid. A phospholipase A1 as used herein may also cleave a lysophospholipid at the SN1 position forming a glycerophosphate and a fatty acid. The wording "phospholipase A1" and a "polypeptide having phospholipase A1 activity" is used interchangeably herein. A polypeptide having phospholipase A1 activity as disclosed herein does not have phospholipase A2 activity.

Incubating an oil with a polypeptide having phospholipase A1 activity in a process as disclosed herein comprises converting phospholipids in the oil into lysophospholipids, and free fatty acids. Incubating an oil with a polypeptide having phospholipase A1 activity in a process as disclosed herein may further comprise converting phospholipids and/or lysophospholipids in the oil into lysophospholipids and/or glycerophosphates, and free fatty acids.

Incubating an oil with a polypeptide having phospholipase A1 activity in a process as disclosed herein can be performed at a pH value of from 2 to 8, for instance from 3 to 7, for instance from 4 to 6.

Incubating an oil with a polypeptide having phospholipase A1 activity can be performed in the presence of an acid. Accordingly, a process for reducing an amount of intact phospholipids in a triacylglyceride oil as disclosed herein comprises adding an acid such that the amount of acid in the oil is from 100 to 1000 ppm of acid, such as from 200 to 900 ppm of acid, for instance from 300 to 800 ppm of acid, for instance from 400 to 600 ppm of acid. A suitable acid used in a process as disclosed herein may comprise citric acid, phosphoric acid, acetic acid, tartaric acid, and/or succinic acid, and any suitable mixture thereof.

Usually water is present in a process as disclosed herein. A process as disclosed herein may further comprise adding water to the oil, for instance an amount of water is added such that an amount of 0.5 to 5 wt %, such as an amount of 1 to 4 wt %, such as an amount of 2 to 3 wt % of water is present in the oil in a process as disclosed herein.

Incubating an oil with a polypeptide having phospholipase A1 activity can be performed at a temperature of from 40° C. to 75° C., for instance a temperature of from 45° C. to 70° C. such as a temperature of from 50 to 65° C.

A suitable period for incubating an edible oil with a phospholipase A1 in a process as disclosed herein is from 0.5 to 10 hrs, such as from 1 to 8 hrs, or from 2 to 6 hrs.

The oil is incubated with a suitable amount of phospholipase A1. A suitable amount of phospholipase is such that at least 80%, 81%, 82%, 83%, 84%, 85%, 86%, 87%, 88%, 89%, or at least 90%, 91%, 92%, 93%, 94% or at least 95% of the amount of intact phospholipids originally present in a triacylglyceride oil is reduced after 4 hours of incubation at a temperature of from 55° C. to 70° C. For instance, an amount of 0.02 to 3 mg active PLA1 protein/kg oil, for instance between 0.05 to 1 mg active PLA1 protein/kg oil, for instance between 0.1 to 0.8 mg active PLA1 protein/kg oil, for instance from 0.15 to 0.5 mg active PLA1 protein/kg oil, for instance from 0.2 to 0.4 mg active PLA1 protein/kg oil A phospholipase A1 may be derived from any suitable organism, for instance from fungi. Suitable fungi include filamentous fungi, such as *Aspergillus, Talaromyces, Trichoderma*, and yeast such as *Pichia, Saccharomyces*, for instance *Aspergillus oryzae, Aspergillus niger, Aspergillus nidulans, Talaromyces emersonii, Pichia pastoris, Saccharomyces cerevisiae*. A polypeptide having phospoplipase A1 activity may be derived from *Aspergillus niger*.

A phospholipase A1 used in a process as disclosed herein may comprise a polypeptide having at least 80% identity to the mature amino acid sequence of SEQ ID NO: 1, such as at least 85%, 90%, 95%, 96%, 97%, 98%, or at least 99% identity to the mature amino acid sequence of SEQ ID NO: 1. A polypeptide having phospholipase A1 activity may comprise or contain the mature amino acid sequence of SEQ ID NO: 1. The mature amino acid sequence of SEQ ID NO: 1 comprises or contains amino acids 30 to 298 of SEQ ID NO: 1. The mature amino acid sequence of SEQ ID NO:1 may also comprise or contain amino acids 29 to 297 of SEQ ID NO: 1, for instance amino acids 28 to 296 of SEQ ID NO: 1, for instance amino acids 31 to 298 of SEQ ID NO: 1, for instance amino acids 32 to 297 of SEQ ID NO: 1. The mature amino acid sequence may also comprise one or more further amino acids at the C-terminus of SEQ ID NO: 1.

A phospholipase A1 used in a process as disclosed herein may be a natural occurring polypeptide or a variant polypeptide.

A phospholipase A1 may be produced in any suitable host cell useful for producing a polypeptide having phospholipase A1 activity as disclosed herein for instance a prokaryotic or eukaryotic cell. A eukaryotic host cell may be a mammalian, insect, plant or fungal cell.

A fungal cell may for instance be a yeast cell or a filamentous fungus cell, for instance a *Saccharomyces* sp. *Pichia, Aspergillus* sp. *Trichoderma* sp., such as *Saccharomyces cerevisiae, Pichia pastoris, Aspergillus niger, Aspergillus oryzae, Trichoderma reesei* or *Trichoderma viride* cell. Molecular biology techniques known to a skilled person are performed according to Sambrook & Russell, Molecular Cloning: A Laboratory Manual, 3rd Ed., CSHL Press, Cold Spring Harbor, NY, 2001.

A host cell useful for producing a phospholipase A1 as disclosed herein is cultivated in a suitable fermentation medium that allows expression of the phospholipase A1. A person skilled in the art knows how to perform a process for preparing a polypeptide having phospholipase A1 activity depending on the host cell used. A suitable fermentation medium usually comprises a carbon and a nitrogen source. Usually a fermentation medium has a pH value of between 4 and 8. A suitable temperature at which a host cell is cultivated is usually between 25 and 60° C. The phospholipase A1 can be recovered from the fermentation medium by methods known in the art, for instance by centrifugation, filtration and/or ultrafiltration.

A phospholipase A1 in a process as disclosed herein may be a composition comprising the phospholipase A1 as disclosed herein, for instance an aqueous composition or a solid composition comprising a phospholipase A1 as disclosed herein. A composition may be a fermentation broth, such as a fermentation broth from which cells and/or other components have been removed, for instance by centrifugation, filtration or ultrafiltration.

A phospholipase A1 may also be a pure or an isolated phospholipase A1, i.e. a polypeptide having phospholipase A1 activity that is removed from at least one component eg. other polypeptide material with which it is naturally associated.

Phospholipids in a triacylglyceride oil comprise phosphatidic acid (PA), phosphatidyl ethanolamine (PE), phosphatidyl inositol (PI), and phosphatidylcholine (PC). Surprisingly it was found that the content or the amount of these four phospholipids was reduced in a process as disclosed herein.

In one embodiment a process as disclosed herein comprises a step of adding an acid to the oil. A suitable acid that can be added to the oil comprises citric acid, phosphoric acid, acetic acid, tartaric acid, and/or succinic acid, and any suitable mixture thereof.

In yet another embodiment, a process as disclosed herein comprises adding a caustic to the oil. A suitable caustic may for instance be potassium hydroxide, or sodium hydroxide, sodium silicate, sodium carbonate, calcium carbonate, sodium bicarbonate, ammonia, sodium citrate or any suitable combination thereof.

Adding an acid, water and/or caustic may be performed during any suitable step in a process for reducing an amount of intact phospholipids in a triacylglyceride oil as disclosed herein. Adding an acid, water and/or caustic may be performed before, during or after incubating the oil with the phospholipase. Preferably, adding acid, water and/or caustic is performed before incubating the oil with a phospholipase A1. Adding caustic can be performed before or after adding acid, for instance adding caustic can be performed after adding acid.

A process for reducing an amount of intact phospholipids in a triacylglyceride oil as disclosed herein may further comprise a step of preconditioning the oil in the presence of an acid and/or a caustic. An acid and/or a caustic is/are as defined herein above. Preconditioning comprises incubating the oil in the presence of an acid and/or a caustic at a temperature of 50° C. to 75° C., for instance a temperature of from 55° C. to 70° C. Preconditioning may be performed during from 1 min to 2 hr, for instance from 5 min to 1 hr, for instance from 10 min to 40 min.

In one embodiment a process as disclosed herein, further comprises incubating the oil with an enzyme having phospholipase C activity, an enzyme having phosphatidylinositol (PI)-phospholipase C activity and/or an enzyme having phospholipase A2 activity.

A phospholipase C (PLC) may be an enzyme from enzyme classification number EC 3.1.4.3 that cleaves phospholipids between the phosphate and the glycerol group, resulting in a diglyceride and a phosphate compound such as choline phosphate or ethanolamine phosphate. A PLC is for instance known from WO2005/086900, WO2012/062817 or WO2016/162456. A PLC may be a polypeptide comprising the amino acid sequence of SEQ ID NO: 3, which is also disclosed on p. 196 of WO2005/086900. A phospholipase C may be a polypeptide which has least 80%, 85%, 90%, 95%, 96%, 97%, 98%, or at least 99% identity to the amino acid sequence of SEQ ID NO: 3.

A phospholipase C may also be a phosphatidylinositol phospholipase C (PI-PLC). A PI-PLC has a preference of cleaving phosphatidylinositol and may also act on other phospholipids such as phosphatidylcholine and phosphatidylethanolamine. Bacterial PI-PLC belongs to enzyme classification EC 4.6.1.13. A suitable PI-PLC enzyme is for instance disclosed in WO2011/046812. A suitable PI-PLC may comprise the amino acid sequence of SEQ ID NO: 4, which corresponds to SEQ ID NO: 8 disclosed in WO2011/046812. A phosphatidyl inositol phospholipase C may be a polypeptide which has least 80%, 85%, 90%, 95%, 96%, 97%, 98%, or at least 99% identity to the amino acid sequence of SEQ ID NO: 4.

A phospholipase A2 (PLA2) releases fatty acids from the second carbon group of glycerol and belongs to enzyme classification EC 3.1.1.4. PLA2 may for instance be pig pancreas PLA2, which may be expressed in a suitable host organism for instance an *Aspergillus* species, such as *Aspergillus niger*.

A process as disclosed herein may further comprise separating phosphorous-containing components from the oil. Separating phosphorous containing components may be performed by any suitable method known in the art for instance by centrifugation. Phosphorous-containing components comprise phospholipids, lysophospholipids and glycerophosphates.

Any suitable triacylglyceride oil may be present or used in a process for reducing the phospholipids in an edible oil in a process as disclosed herein. A triacylglyceride oil may be a crude edible oil or a water degummed edible oil. Crude oil, also called non-degummed oil, refers to a pressed or extracted oil. The oil may be a vegetable or plant oil, animal oil, fish oil, or algal oil. A vegetable oil may be any suitable oil for instance soy bean oil, rapeseed oil, canola oil, sunflower oil, palm oil, palm kernel oil, coconut oil, sesame oil, olive oil, rice bran oil, cotton seed oil, corn oil, nuts oil, such as almond, walnut, peanut oil or a mixture thereof. A process for reducing an amount of intact phospholipids in a triacylglyceride oil can also be indicated as an oil degumming or as an oil refining process.

A crude vegetable oil may comprise between 1 and 2000 ppm such as between 1 and 1000 ppm of atomic phosphorous. The amount of atomic phosphorous is indicative for the amount of phospholipids.

Also disclosed herein is a triacylglyceride oil comprising a polypeptide having phospholipase A1 activity, wherein the polypeptide comprises a polypeptide having at least 80% identity to the mature amino acid sequence of SEQ ID NO: 1. A triacylglyceride oil may be obtainable by a process as disclosed herein. All embodiments disclosed herein above for a process as disclosed herein are applicable for the triacylglyceride oil as disclosed herein.

An oil as disclosed herein may further comprise a polypeptide having phospholipase C activity, a polypeptide having phosphatidylinositol phospholipase C activity (PI-PLC), and/or a polypeptide having phospholipase A2 activity. An oil as disclosed herein may further comprise a polypeptide having phospholipase C activity which has at least 80%, 85%, 90%, 95%, 96%, 97%, 98%, or at least 99% identity to the amino acid sequence of SEQ ID NO: 3, a polypeptide having phosphatidyl inositol phospholipase C activity which has at least 80%, 85%, 90%, 95%, 96%, 97%, 98%, or at least 99% identity to the amino acid sequence of SEQ ID NO: 4 and/or a phospholipase A2 from pig pancreas.

FIGURE

FIG. 1. Schematic presentation of the pGBTOPPLA-1 plasmid used for the expression of the *A. niger* PLA1 enzyme.

EXAMPLES

Materials and Methods

Molecular Biology Techniques

Molecular biology techniques known to a skilled person are performed according to Sambrook & Russell, Molecular Cloning: A Laboratory Manual, 3rd Ed., CSHL Press, Cold Spring Harbor, NY, 2001. Polymerase chain reaction (PCR) is performed on a thermocycler with Phusion High-Fidelity DNA polymerase (Finnzymes OY, Aspoo, Finland) according to the instructions of the manufacturer.

Enzymes

Purifine® PLC/PI-PLC is an enzymes mixture comprising a phospholipase C (SEQ ID NO 3), and a phosphatidylinositol phospholipase C (SEQ ID NO: 4). Purifine® 3G an enzymes mixture comprising a phospholipase C (SEQ ID NO: 3), a phosphatidylinositol phospholipase C (SEQ ID NO: 4) and a phospholipase A2 (pig pancreas PLA2) are commercially available from DSM.

Lecitase® Ultra from Novozymes, a phospholipase A from *Fusarium oxysporum*, was from Sigma Aldrich.

Rohalase® PL XTRA, a phospholipase A from *Aspergillus fumigatus* was obtained from AB Enzymes.

Strain Construction

An *A. niger* strain (deposited at the CBS Institute under the deposit number CBS 513.88) comprising a deletion of the gene encoding glucoamylase (glaA) and a deletion of the pepA gene was constructed according to the approach as described in EP 0635574 B1 and van den Hombergh et al. (1997) Eur J Biochem. 247(2): 605-13), respectively. Subsequently, an oxalate deficient *A. niger* strain was constructed from the *A. niger* strain comprising ΔglaA, ΔpepA, according to the approach described in WO2004/070022, resulting in an *A. niger* comprising a deletion of the glaA, pepA and oahA gene (ΔglaA, ΔpepA, ΔoahA).

Construction of PLA1 Producing *Aspergillus niger* Strains

The *A. niger* PLA1 enzyme (with a coding sequence as depicted in SEQ ID NO: 2, and a protein sequence as depicted in SEQ ID NO: 1 was selected for enzyme expression in the *A. niger* (ΔglaA, ΔpepA, ΔoahA) strain.

The PLA1-encoding gene was made by gene synthesis and cloned into an *A. niger* pGBTOP-12 expression vector using the techniques as described in WO 98/46772 and WO 99/32617, under the control of the glucoamylase promoter, yielding an *A. niger* pGBTOPPLA-1 expression vector (Figure), using the same techniques as described in WO 98/46772 and WO 99/32617.

Enzyme producing strains for PLA1 enzyme were constructed by co-transformation of the *A. niger* (ΔglaA, ΔpepA, ΔoahA) strain, with the amdS selectable marker-gene containing vector pGBAAS-1 and the pGBTOPLA-1 vector and subsequent selection of transformants. The transformation and counterselection procedure (as described in WO98/46772 and WO99/32617), followed by selection of strains resulted in (multicopy) strains producing PLA1 protein. From all pGBTOPPLA-1 transformants, 1 high-copy enzyme-producing strain within the (ΔglaA, ΔpepA, ΔoahA) background was selected, further replica-plated to obtain a single strain inoculum and named strain PLA1-1. The PLA1-1 strain was used as the respective PLA1 producing strain in subsequent experiments.

*A. niger* Shake Flask Fermentations for PLA1 Production

Fresh *A. niger* PLA1-1 spores were prepared. Four 100 ml shake flasks with 20 ml fermentation medium 1 (10% w/v Corn Steep Solids, 1% w/v glucose.H$_2$O, 0.1% w/v NaH$_2$PO$_4$·H$_2$O, 0.05% w/v MgSO$_4$·7H$_2$O, 0.025% w/v Basildon, pH 5.8) in 500 ml shake flasks with baffle were inoculated with 107 spores. These pre-cultures were incubated at 34° C. and 170 rpm for 16-24 hours. From the pre-cultures, 10-15 ml was used for inoculation of 500 ml shake flasks with 100 ml fermentation medium 2 (15% w/v maltose, 6% w/v bacto-soytone, 1.5% w/v (NH$_4$)$_2$SO$_4$, 0.1% w/v NaH$_2$PO$_4$·H$_2$O, 0.1% w/v MgSO$_4$·7H$_2$O, 0.1% w/v L-arginine, 8% w/v Tween-80, 2% w/v Basildon, 2% w/v MES pH 5.1) at 34° C. and 170 rpm. After seven days of cultivation, the cells were killed off by adding 3.5 g/l of sodium benzoate and keeping at 30° C. for six hours. Subsequently, 10 g/l CaCl$_2$ and 45 g/l Perlite C25 was added to the culture broth. Filtration was carried out in one step using filter cloth and filters DE60/EKS P and K250 (Pall). The filter cake remaining at the filter was washed with 1.1 l of sterile milliQ water. Subsequent sterile filtration was carried out using 0.22 m GP Express PLUS Membrane (Millipore). The filtrate comprising PLA1 was used in the examples.

Phospholipase A1 (PLA1) Activity Assay

The following solutions were prepared:
1) Substrate solution: 1 g L-α-phosphatidylcholine from egg yolk (Sigma P3556, Zwijndrecht, the Netherlands) in 2% triton X-100 solution.
2) 0.2 M acetate buffer pH 4.5
3) Stop solution: 1 M HCl A mixture of 500 μL solution 1 and 300 μL solution 2 was equilibrated at 37° C. The reaction was started by adding 100 μL enzyme solution with activity between 0.05-1.0 U/mL. After 10 min incubation at 37° C. the reaction was stopped by adding 100 μL solution 3. A blank measurement was additionally done by incubating the substrate without sample for 10 minutes at 37° C. After adding 100 μL of the stop reagent, 100 μL sample was added. The amount of free fatty acid formed in sample and blank was determined by following the instructions described in the package insert of the Wako HR series NEFA-HR (2) diagnostic kit (wakodiagnostics.com/r_nefa.html). Activity is calculated as follows:

$$U/mL = \frac{\Delta FFA \times Vt \times df}{Vs \times t}$$

ΔFFA=FFA in sample—FFA in blank (μmol/mL)
Vt=total volume after stopping the reaction (1 mL)
Vs=sample volume (0.1 mL)
t=incubation time (10 minutes)
df=dilution factor of sample 1 U is defined as the amount of enzyme that liberates one micromole of free fatty acid per minute under the conditions of the test.

Phospholipase C (PLC) Activity Assay

The substrate solution consisted of 10 mM pNP-nitrophenyl phosphorylcholine (article N83020 from Melford Laboratories Ltd, Ipswich, United Kingdom), 100 mM MOPS buffer pH 7.3, 0.2% Triton X-100 and 1 mM ZnSO$_4$. A mixture of 40 μL sample (with activity between 0.03-0.1 U/mL) and 960 μL substrate solution was incubated at 37° C. for 30 min. The reaction was stopped by adding 1000 μL stop reagent containing 1 M TRIS and 50 mM EDTA adjusted to pH 10 with 0.5 M NaOH. A blank was made by adding the stop reagent before the enzyme sample. The optical density (OD) of samples and blanks were measured at 405 nm.

Calibration was performed by preparing pNP solutions of respectively 0-0.5-1.0-2.0-2.9-4.0 mM in above mentioned buffer. 40 µL of each standard solution was mixed with 960 µL substrate and 1000 µL stop reagent. The OD of each solution was measured at 405 nm. By using linear regression, the slope of the calibration line was calculated.

Activity was calculated by using the following formula:

$$U/mL = \frac{\Delta Abs \times df}{t * slope}$$

$\Delta Abs = (A_{sample} - A_{blank})$
df=dilution factor of sample
slope=slope of p-nitro-phenol calibration curve (mL/µmol)
t=incubation time assay (30 min)

One unit is defined as the amount of enzyme that liberates 1 µmol p-nitrophenol per minute under the conditions of the test (pH 7.3, 37° C.).

Phosphatidyl-Inositol Phospholipase (PI-PLC) Activity Assay

The substrate solution consisted of 20 mM 4-Methylumbelliferyl myo-inositol-1-phosphate, N-methyl-morpholine (BioSynth M-5717, Brussels, Belgium) dissolved in 200 mM Na-phosphate buffer pH 7.5 also containing 0.1% triton X-100. 140 µL substrate was equilibrated at 37° C. Reaction was started by adding 10 µL of sample with activity between 0.2 and 1.0 U/mL. While incubating at 37° C. the change in absorption was measured at 380 nm against a sample blank. The slope (deltaOD/time) of the linear part of the curve is used as a measure for the activity.

Calibration was performed by preparing 4-Methylumbelliferone solutions of respectively 0-1.0-2.0-3.0-4.0-5.0 mM in 200 mM phosphate buffer. 10 µL of each standard solution was mixed with 140 µL substrate. The OD of each solution was measured at 380 nm. By using linear regression, the slope of the calibration line was calculated.

Activity was calculated by using the following formula: $U/mL = (\Delta Abs/min_{sample} - \Delta Abs/min_{blanc}) \times df/S$ $\Delta Abs/min_{sample}$=absorbance change per min of sample
$\Delta Abs/min_{blanc}$=absorbance change per min of buffer blank
df=dilution factor of sample
S=slope of 4-Methylumbelliferone calibration curve [mL/µmole]

One unit is defined as the amount of enzyme that liberates 1 µmole of 4-methylumbelliferone from 18.7 mM 4-Methylumbelliferyl myo-inositol-1-phosphate during in one minute at pH 7.5 and 37° C.

Quantitative Determination of Phospholipids, Lysophospholipids, and Glycerophosphate Content Using $^{31}P$ NMR 500-1000 mg oil was weighed accurately into a suitable vial, and approximately 10 g cold acetone was added and mixed thoroughly. The oil-acetone mixture was kept at 4° C. for at least 30 min, and then centrifuged for 10 min at 3000 rpm, after which the liquid phase was discarded. The pellet is resuspended in 500 µl buffer (containing 25 g L-1 deoxycholic acid, 5.84 g L-1 EDTA, and 10.9 g L-1 TRIS, buffered using KOH at pH 9.0), and 50 µL of an internal standard solution (containing 10 g L-1 triisopropylphosphate in extraction buffer) was added.

1D $P^{31}$ NMR spectra were recorded on a Bruker Avance III HD spectrometer, operating at a 31P frequency of 161.97 MHz equipped with a nitrogen cooled cryoprobe, at sample temperature of 300K. An inverse gated pulse program (ZGIG) with Waltz16 proton decoupling was used, recording 4 dummy scans, and 128 scans per spectrum, using a 90-degree pulse. An acquisition time of 3.37 s, and a relaxation delay of 11.5 s was used.

The analyte concentrations were calculated relative to triisopropylphosphate.

A correction factor was applied to correct for the incomplete relaxation of cholinephosphate and ethanolaminephosphate.

Quantitative Determination of Diacylglycerol (DAG) in Oils

Neutral lipid classes were separated with normal-phase high-performance liquid chromatography (HPLC), and the diglycerides present were determined with an evaporative light scattering detector (ELSD). This method has been modified from the official AOCS method Cd 11 d-96. The content is expressed as percentage (wt %).

Example 1. Crude Soybean and Rapeseed Oil Degumming at 55-70° C. Using PLA1

Two crude soybean oils from American oil seed processors and two rapeseed oils from European oil seed processors were used. 10 g oil was weighed into a vial, and heated to 70° C., after which citric acid (as 50% solution) was added into the oil until the end citric acid concentration in oil was 500 ppm. The vial that contains citric acid conditioned oil was incubated at 70° C. for at least 30 min.

After incubation, the temperature was adjusted and kept at 55, 60, 65 and 70° C. When the temperature was stable PLA1 produced as described above (0.28 mg active protein/kg oil (1.25 PLA Unit/g)) and water were mixed into the oil using Ultra Turrax. the final water concentration in oil was 3 wt %. The reaction went on for 4 hours while the oil was kept mixed with a magnetic stirrer at 800 ppm. Samples were taken after 4 h incubation and the phospholipid (PL) content, i.e. phosphatidic acid (PA), phosphatidyl choline (PC), phosphatidyl ethanolamine (PE), and phosphatidyl inositol (PI), analysis using $^{31}P$-NMR as described above.

The results in Tables 1 to 4 below show that a PLA1 as disclosed herein reduced the content of all four phospholipids PA, PC, PE and PI. More than 85% of the total amount of phospholipids (PL) originally present in the oil was hydrolyzed at temperature of 55° C., 60° C., 65° C. and 70° C. after 4 hours of reaction.

TABLE 1

Phospholipid content in crude soybean oil before and after incubation with phospholipase A1.
Crude soybean oil A

| | PA | PC | PE | PI | Total PL |
|---|---|---|---|---|---|
| | | | µmol/100 g oil | | |
| time 0 | 207.0 | 901.0 | 603.2 | 499.7 | 2211.0 |
| 55° C., 4 h | 15.5 | 28.7 | 18.7 | 19.6 | 82.4 |
| 60° C., 4 h | 18.5 | 47.3 | 20.0 | 27.7 | 113.5 |
| 65° C., 4 h | 17.9 | 46.3 | 21.6 | 26.1 | 111.9 |
| 70° C., 4 h | 31.6 | 81.4 | 23.8 | 43.7 | 180.5 |

TABLE 2

Phospholipid content in crude soybean oil before
and after incubation with phospholipase A1.
Crude soybean oil B

|  | PA | PC | PE | PI | Total PL |
|---|---|---|---|---|---|
|  |  | μmol/100 g oil |  |  |  |
| time 0 | 179.9 | 450.5 | 374.0 | 285.1 | 1289.5 |
| 55° C., 4 h | 14.7 | 21.4 | 17.7 | 13.4 | 67.2 |
| 60° C., 4 h | <10 | 15.2 | 19.0 | <10 | 34.2 |
| 65° C., 4 h | 19.3 | 27.8 | 19.3 | 17.5 | 83.9 |
| 70° C., 4 h | 18.2 | 29.7 | 21.4 | 17.5 | 86.7 |

TABLE 3

Phospholipid content in crude rapeseed oil before
and after incubation with phospholipase A1.
Crude rapeseed oil A

|  | PA | PC | PE | PI | Total PL |
|---|---|---|---|---|---|
|  |  | μmol/100 g oil |  |  |  |
| time 0 | 477.4 | 762.3 | 334.0 | 444.2 | 2017.9 |
| 55° C., 4 h | 43.7 | 29.2 | 29.8 | 21.2 | 123.8 |
| 60° C., 4 h | 49.3 | 41.3 | 31.0 | 24.2 | 145.8 |
| 65° C., 4 h | 58.8 | 42.2 | 29.7 | 24.2 | 154.9 |
| 70° C., 4 h | 63.5 | 53.4 | 22.0 | 32.7 | 171.5 |

TABLE 4

Phospholipid content in crude rapeseed oil before
and after incubation with phospholipase A1.
Crude rapeseed oil B

|  | PA | PC | PE | PI | Total PL |
|---|---|---|---|---|---|
|  |  | μmol/100 g oil |  |  |  |
| time 0 | 500.9 | 350.1 | 247.3 | 235.0 | 1333.2 |
| 55° C., 4 h | 18.5 | <10 | 18.2 | <10 | 36.7 |
| 60° C., 4 h | 24.2 | <10 | 16.0 | <10 | 40.3 |
| 65° C., 4 h | 27.7 | 11.0 | 18.2 | <10 | 56.8 |
| 70° C., 4 h | 84.4 | 26.3 | 13.7 | 17.6 | 142.0 |

Example 2. Performance Comparison Between PLA1 and Commercial Phospholipase A at 55° C.

Crude soybean oil and water degummed soybean oil from American oil seed processors were used. 10 g oil was weighed into a vial, and heated to 70° C., after which citric acid (as 50% solution) was added into the oil until the end citric acid concentration in oil was 500 ppm. The vial that contained citric acid conditioned oil was incubated at 70° C. for at least 30 min, and subsequently the temperature was adjusted and kept at 55° C.

When the temperature was stable, 25 ppm of PLA1 produced as described above and water were mixed into the oil using Ultra Turrax. The final water concentration in oil was 3 wt %.

Before incubating the oil that was treated with citric acid and adjusted to 55° C. as described above with Lecitase® Ultra phospholipase A and Rohalase® PL XTRA phospholipase A, 2M NaOH was first added into the oil until a final concentration of 138 ppm NaOH in oil was reached. Then 25 ppm of the commercial enzymes and water were mixed into the oil using Ultra Turrax, the end water concentration in oil was 3 wt %.

After 4 h incubation at 55° C. while mixing with a magnetic stirrer at 800 ppm samples were taken and the phospholipid content, i.e. phosphatidic acid (PA), phosphatidyl choline (PC), phosphatidyl ethanolamine (PE), and phosphatidyl inositol (PI), the lysophospholipid content, i.e. lyso-PA (LPA), lyso-PC (LPC), lyso-PE (LPE), and lyso-PI (LPI), and the glycerophosphate content, i.e. glycerol-PA (GPA), glycerol-PC (GPC), glycerol-PE (GPE), and glycerol-(GPI) were determined using $^{31}$P-NMR as described above.

The results in Tables 5 and 6 show that the PLA1 as disclosed herein reached a lower level of phospholipids PA, PC, PE and PI after 4 hours of reaction in both crude and water degummed soybean oil, at 55° C. with 25 ppm dosage than the two commercial enzymes Lecitase® Ultra and Rohalase® PL XTRA, under their optimal reaction conditions. In addition, the results in Table 5 and 6 show that PLA1 as disclosed herein shows lyso-phospholipase activity, and converts all 4 lysophospholipids into glycerophosphate in both crude and water degummed soybean oil in a higher amount than the two commercial enzymes, Lecitase® Ultra and Rohalase® PL XTRA at 55° C. As the emulsification capacity of glycerophosphate is lower than lysophospholipid, converting lysophospholipid to glycerophosphate can therefore enhance the efficiency of oil-gum separation in the centrifugation step.

TABLE 5

Phospholipid, lysophospholipid, and glycerophosphate content in crude soybean oil
before and after incubation with different phospholipases at 55° C. for 4 hr
Crude Soybean Oil

|  | PA | PC | PE | PI | Total PL | LPA | LPC | LPE | LPI | GPA | GPC | GPE | GPI |
|---|---|---|---|---|---|---|---|---|---|---|---|---|---|
|  |  |  |  |  | μmol/100 g oil |  |  |  |  |  |  |  |  |
| time 0 | 250 | 561 | 543 | 344 | 1699 | 106 | 132 | 83 | < | < | < | < | < |
| PLA1 | < | 57 | < | < | 57 | 204 | 478 | 389 | 265 | 140 | 228 | 164 | 87 |
| Lecitase ® Ultra | < | 101 | 52 | 149 | 302 | 257 | 525 | 403 | 173 | 57 | 62 | 73 | < |
| Rohalase ® PL XTRA | 114 | 201 | 163 | 121 | 599 | 245 | 517 | 382 | 255 | < | 48 | < | < |

TABLE 6

Phospholipid, lysophospholipid, and glycerophosphate content in water degummed soybean oil before and after incubation with different phospholipases at 55° C. for 4 hr
Water degummed soybean oil

| | PA | PC | PE | PI | Total PL | LPA | LPC | LPE | LPI | GPA | GPC | GPE | GPI |
|---|---|---|---|---|---|---|---|---|---|---|---|---|---|
| | | | | | | | μmol/100 g oil | | | | | | |
| time 0 | 123 | 191 | 134 | 100 | 547 | < | 59 | < | < | < | < | < | < |
| PLA1 | < | < | < | < | 0 | 93 | 148 | 99 | 71 | 41 | 72 | 48 | < |
| Lecitase ® Ultra | < | < | < | 52 | 52 | 107 | 179 | 110 | 75 | < | < | < | < |
| Rohalase ® PL XTRA | < | < | < | < | 0 | 96 | 155 | 97 | 85 | < | < | < | < |

Example 3. Performance Comparison Between PLA1 and Commercially Available Phospholipase a in Crude Soybean Oil at a Temperature of 55, 60 and 65° C.

Crude soybean oil from American oil seed processors was used. 10 g oil was weighed into a vial, and heated to 70° C., after which citric acid (as 50% solution) was added into the oil until the end citric acid concentration in oil was 500 ppm. The vial that contained citric acid conditioned oil was incubated at 70° C. for at least 30 min.

After incubation, the temperature was adjusted and kept at 55° C., 60° C., and 65° C. When the temperature was stable, PLA1 (0.25 mg active protein/kg oil) produced as described above, and water were mixed into the oil using Ultra Turrax. The final water concentration in oil was 3 wt %.

For the comparison with Lecitase® Ultra and Rohalase® PL XTRA, 2M NaOH was first added into the citric acid conditioned oil until a final concentration of 138 ppm NaOH in oil was reached, to obtain the optimal condition for these enzymes. Subsequently, Lecitase® Ultra or Rohalase® PL XTRA (0.25 mg active protein/kg oil) and water were mixed into the oil using Ultra Turrax. The end water concentration in oil was 3 wt %.

The reaction went on for 4 hours while the oil was kept mixed with a magnetic stirrer at 800 ppm. Samples were taken after 4 h incubation and the phospholipid content, i.e. phosphatidic acid (PA), phosphatidyl choline (PC), phosphatidyl ethanolamine (PE), and phosphatidyl inositol (PI), analysis using $^{31}$P-NMR as described above.

The results in Tables 7 to 9 below show that the *A. niger* PLA1 as disclosed herein reached a lower level of phospholipids PA, PC, PE and PI at 55° C., 60° C., 65° C. after 4 hours of reaction in crude soybean oil, than the commercial enzymes Lecitase® Ultra, and Rohalase® PL XTRA under their optimal reaction conditions.

TABLE 7

Phospholipid content in crude soybean oil before and after incubation with different phospholipases for 4 hr
Crude soybean oil, 55° C.

| | PA | PC | PE | PI | Total PL |
|---|---|---|---|---|---|
| | | μmol/100 g oil | | | |
| time 0 | 215 | 506 | 459 | 315 | 1495 |
| PLA1 | 14 | 20 | 18 | 13 | 65 |
| Lecitase ® Ultra | < | 101 | 52 | 149 | 302 |
| Rohalase ® PL XTRA | 22 | 68 | 42 | 35 | 167 |

<: not detected

TABLE 8

Phospholipid content in crude soybean oil before and after incubation with different phospholipases for 4 hr
Crude soybean oil, 60° C.

| | PA | PC | PE | PI | Total PL |
|---|---|---|---|---|---|
| | | μmol/100 g oil | | | |
| time 0 | 215 | 506 | 459 | 315 | 1495 |
| PLA1 | < | 15 | 19 | < | 34 |
| Lecitase ® Ultra | 101 | 448 | 406 | 295 | 1250 |
| Rohalase ® PL XTRA | 23 | 71 | 48 | 31 | 174 |

<: not detected

TABLE 9

Phospholipid content in crude soybean oil before and after incubation with different phospholipases for 4 hr
Crude soybean oil, 65° C.

| | PA | PC | PE | PI | Total PL |
|---|---|---|---|---|---|
| | | μmol/100 g oil | | | |
| time 0 | 215 | 506 | 459 | 315 | 1495 |
| PLA1 | 19 | 28 | 19 | 17 | 84 |
| Rohalase ® PL XTRA | 25 | 84 | 46 | 34 | 189 |

Example 4. Performance Comparison Between PLA1 and Commercially Available Phospholipase a in Water Degummed Soybean Oil at a Temperature of 55, 60 and 65° C.

Water degummed soybean oil from American oil seed processors was used. 10 g oil was weighed into a vial, and heated to 70° C., after which citric acid (as 50% solution) was added into the oil until the end citric acid concentration in oil was 500 ppm. The vial that contains citric acid conditioned oil was incubated at 70° C. for at least 30 min.

After incubation, the temperature was adjusted and kept at 55° C., 60° C., and 65° C. When the temperature was stable, PLA1 (0.25 mg active protein/kg oil) produced as described above, and water were mixed into the oil using Ultra Turrax. The final water concentration in oil was 3 wt %.

For the comparison with Lecitase® Ultra and Rohalase® PL XTRA, 2M NaOH was first added into the citric acid conditioned oil until a final concentration of 138 ppm NaOH in oil was reached to obtain the optimal condition for these enzymes. Subsequently, Lecitase® Ultra or Rohalase® PL XTRA (0.25 mg active protein/kg oil) and water were mixed into the oil using Ultra Turrax. The end water concentration in oil was 3 wt %.

The reaction went on for 4 hours while the oil was kept mixed with a magnetic stirrer at 800 ppm. Samples were taken after 4 h incubation and the phospholipid content, i.e. phosphatidic acid (PA), phosphatidyl choline (PC), phosphatidyl ethanolamine (PE), and phosphatidyl inositol (PI), was determined using $^{31}$P-NMR as described above.

The results in Tables 10 to 12 show that the PLA1 as disclosed herein reached a lower level of phospholipids PA, PC, PE and PI in water degummed soybean oil, at 55-65° C., after 4 hours of reaction than the commercial enzyme Lecitase® Ultra, while Rohalase® PL XTRA also resulted in a low phospholipids level at 600° C. and 65° C., under the optimal reaction conditions of the three enzymes.

TABLE 10

Phospholipid content in water degummed soybean oil before and after incubation with different phospholipases for 4 hr Water degummed soybean oil, 55° C.

| | PA | PC | PE | PI | Total PL |
|---|---|---|---|---|---|
| | | | μmol/100 g oil | | |
| time 0 | 228 | 132 | 155 | 146 | 661 |
| PLA1 | 25 | < | 9 | < | 34 |
| Lecitase ® Ultra | 18 | < | 15 | 20 | 53 |
| Rohalase ® PL XTRA | 26 | < | 11 | < | 36 |

<: not detected

TABLE 11

Phospholipid content in water degummed soybean oil before and after incubation with different phospholipases for 4 hr Water degummed soybean oil, 60° C.

| | PA | PC | PE | PI | Total PL |
|---|---|---|---|---|---|
| | | | μmol/100 g oil | | |
| time 0 | 228 | 155 | 146 | 132 | 661 |
| PLA1 | 46 | < | 12 | < | 58 |
| Lecitase ® Ultra | 30 | 79 | 67 | 57 | 232 |
| Rohalase ® PL XTRA | 22 | < | 11 | < | 33 |

<: not detected

TABLE 12

Phospholipid content in water degummed soybean oil before and after incubation with different phospholipases for 4 hr Water degummed soybean oil, 65° C.

| | PA | PC | PE | PI | Total PL |
|---|---|---|---|---|---|
| | | | μmol/100 g oil | | |
| time 0 | 228 | 155 | 146 | 132 | 661 |
| PLA1 | 58 | 17 | 14 | 14 | 102 |
| Lecitase ® Ultra | 188 | 62 | 90 | 78 | 418 |
| Rohalase ® PL XTRA | 20 | < | < | < | 20 |

<: not detected

Example 5: Degumming Using PLC/PIPLC and PLA1 Combination

Crude soybean oil and crude rapeseed oil as disclosed in Example 1 were used. 10 g oil was weighed into a vial, which was heated to 70° C. For pre-conditioning, citric acid (50% solution) was added into the oil, the final citric acid concentration in oil was 500 ppm. This oil was incubated at 70° C. for at least 30 min, after which NaOH was added to a concentration of 138 ppm NaOH. After the pre-conditioning, the temperature was adjusted and kept at 55° C.

A mixture of PLA1 produced as disclosed above and Purifine PLC/PI-PLC was added together with water into the oil, and mixed using Ultra Turrax. The dosage of PLA1 is 0.28 mg active protein/kg oil, and the dosage of Purifine PLC/PI-PLC is 0.013 U-PLC/g oil and 0.05 U-PI-PLC/g oil, the final water concentration in oil was 3 wt %.

The reaction was carried out for 4 hours, while the oil was kept mixed with a magnetic stirrer at 800 rpm. After 2 h and 4 h incubation at 55° C., samples were taken for determination of the phospholipid content, namely phosphatidic acid (PA), phosphatidyl choline (PC), phosphatidyl ethanolamine (PE), and phosphatidyl inositol (PI), and reaction products using $^{31}$P-NMR analysis; diglyceride (DAG) was analyzed using HPLC.

The results in Table 13 and 14 show that when using PLA1 simultaneously with PLC/PI-PLC, the intact phospholipid content can be further reduced compared to when using PLC/PI-PLC alone. After 4 hours of PLA1+PLC/PI-PLC reaction, >90% of the phospholipids are hydrolyzed. The formation of diglyceride (DAG) is reduced when PLA1 is used simultaneously with PLC/PI-PLC, but the reduction is limited to 5-15% of the total formed DAG with no pre-conditioning.

TABLE 13

Phospholipid content in crude soybean oil before and after incubation at 55° C. with phospholipase C, PI-PLC and phospholipase A1
Crude soybean oil

| | | PA | PC | PE | PI | Total PL | delta-DAG w/w % |
|---|---|---|---|---|---|---|---|
| | | | | μmol/100 g oil | | | |
| time 0 | | 210 | 547 | 455 | 328 | 1541 | |
| 2 hr | PLC/PI-PLC, no pre-conditioning | 187 | ≤ | 116 | ≤ | 303 | 0.76 |
| | PLC/PI-PLC + PLA1, no pre-conditioning | 65 | ≤ | ≤ | ≤ | 65 | |
| | PLC/PI-PLC, with pre-conditioning | 188 | 50 | 195 | ≤ | 433 | 0.63 |
| | PLC/PI-PLC + PLA1, with pre-conditioning | ≤ | 61 | 48 | ≤ | 109 | |

TABLE 13-continued

Phospholipid content in crude soybean oil before and after incubation at 55° C. with phospholipase C, PI-PLC and phospholipase A1

Crude soybean oil

| | | PA | PC | PE | PI | Total PL | delta-DAG w/w % |
|---|---|---|---|---|---|---|---|
| | | | | μmol/100 g oil | | | |
| 4 hr | PLC/PI-PLC + PLA1, no pre-conditioning | ≤ | ≤ | ≤ | ≤ | ≤ | 0.68 |
| | PLC/PI-PLC + PLA1, with pre-conditioning | ≤ | 41 | 50 | ≤ | 91 | 0.12 |

≤: not detected

TABLE 14

Phospholipid content in crude rapeseed oil before and after incubation at 55° C. with phospholipase C and phospholipase A1

Crude rapeseed oil

| | | PA | PC | PE | PI | Total PL | delta-DAG w/w % |
|---|---|---|---|---|---|---|---|
| | | | | μmol/100 g oil | | | |
| time 0 | | 524 | 718 | 345 | 404 | 1992 | |
| 2 hr | PLC/PI-PLC, no pre-conditioning | 563 | 222 | 286 | ≤ | 1070 | 0.71 |
| | PLC/PI-PLC + PLA1, no pre-conditioning | 327 | 0 | 70 | ≤ | 397 | |
| | PLC/PI-PLC, with pre-conditioning | 584 | 354 | 301 | 72 | 1312 | 0.55 |
| | PLC/PI-PLC + PLA1, with pre-conditioning | 191 | 49 | 42 | ≤ | 282 | |
| 4 hr | PLC/PI-PLC + PLA1, no pre-conditioning | 233 | ≤ | ≤ | ≤ | 233 | 0.68 |
| | PLC/PI-PLC + PLA1, with pre-conditioning | 98 | ≤ | 60 | ≤ | 158 | 0.44 |

≤: not detected

Example 6: Refining Using Purifine® 3G and PLA1

Two crude soybean oils from American oil seed processors were used. 10 g oil was weighed into a vial, which was heated to 60° C.

Purifine® 3G and PLA1 from *A. niger* produced as disclosed above were added either together or in sequential order with water into the oil. After the addition of the enzymes the oil mixture was mixed using Ultra Turrax. When Purifine® 3G and the PLA1 were added together, no pre-conditioning was done. When added in sequential order, first Purifine® 3G was incubated for 2 hours, after which 500 ppm citric acid was added and subsequently PLA1 was added.

The dosage of Purifine® 3G was 0.013 U-PLC/g oil and 0.05 U-PI-PLC/g oil (150-200 ppm), while the dosage of PLA1 was either 0.28 or 0.56 mg active protein/kg oil. The final water concentration in oil was 3 wt %.

The reaction was carried out for 4 hours, while the oil was kept mixed with a magnetic stirrer at 800 rpm. After 2 h and 4 h incubation at 60° C., samples were taken for determination of the phospholipid (PL) content, namely phosphatidic acid (PA), phosphatidyl choline (PC), phosphatidyl ethanolamine (PE), and phosphatidyl inositol (PI), and reaction products using $^{31}$P-NMR analysis as disclosed above. Diglyceride (DAG) was analysed using HPLC disclosed above.

The results in Table 15 and 16 show that when using Purifine® 3G in combination with PLA1, a higher amount of phospholipids was hydrolysed as compared to the use Purifine® 3G alone. In some cases (e.g. crude soybean oil C), no preconditioning was needed for the combination to reach low phosphorous level, while in some other cases (e.g. crude soybean oil D), acid addition prior to PLA1 was needed to reach low phosphorus level. The formation of diglyceride (DAG) was reduced when PLA1 is used in combination with Purifine® 3G, i.e. 5-15% less DAG as compared to the total DAG formed after incubation with Purifine @ 3G alone.

TABLE 15

Phospholipid content in crude soybean oil C before and after incubation at 60° C. with Purifine ® 3G and PLA1. No preconditioning as applied.

Crude soybean oil C

|  |  | PA | PC | PE | PI | Total PL | delta-DAG w/w % |
|---|---|---|---|---|---|---|---|
|  |  | | | µmol/100 g oil | | | |
| time 0 |  | 328 | 1067 | 775 | 592 | 2763 | 0 |
| 2 hr | Purifine ® 3G | 242 | 90 | 356 | 160 | 847 | 1.16 |
|  | Purifine ® 3G + PLA1 (0.28 mg active protein/kg oil) | 96 | < | 57 | < | 152 | 1.01 |
|  | Purifine ® 3G + PLA1 (0.56 mg active protein/kg oil) | 59 | < | < | < | 59 | 0.91 |
| 4 hr | Purifine ® 3G + PLA1 (0.28 mg active protein/kg oil) | 53 | < | < | < | 53 | 1.01 |
|  | Purifine ® 3G + PLA1 (0.56 mg active protein/kg oil) | < | < | < | < | 0 | 0.86 |

<: not detected

TABLE 16

Phospholipid content in crude soybean oil D before and after incubation at 60° C. with Purifine ® 3G and PLA1 (0.28 mg active protein/kg oil in all experiments)

Crude soybean oil D

|  |  | PA | PC | PE | PI | Total PL | delta-DAG w/w % |
|---|---|---|---|---|---|---|---|
|  |  | | | µmol/100 g oil | | | |
| time 0 |  | 376 | 571 | 591 | 308 | 1846 | |
| 2 hr | Purifine ® 3G | 222 | 119 | 228 | < | 569 | 0.56 |
|  | Purifine ® 3G + PLA1 added together | 252 | 69 | 191 | 64 | 576 | 0.50 |
|  | Purifine ® 3G + 500 ppm citric acid + PLA1 added in sequential order | 245 | 74 | 217 | 72 | 609 | 0.52 |
| 4 hr | Purifine ® 3G | 159 | 78 | 162 | < | 399 | 0.63 |
|  | Purifine ® 3G + PLA1 added together | 199 | < | 128 | < | 327 | 0.62 |
|  | Purifine ® 3G + 500 ppm citric acid + PLA1 added in sequential order | < | < | < | < | < | 0.58 |

<: not detected

---

The invention claimed is:

1. A process for reducing an amount of intact phospholipids in a triacylglyceride oil, comprising incubating the oil with a polypeptide having phospholipase A1 activity, wherein the polypeptide comprises a polypeptide having at least 80% identity to a mature amino acid sequence of SEQ ID NO: 1.

2. The process according to claim 1, wherein the mature amino acid sequence of SEQ ID NO: 1 comprises amino acids 30 to 298 of SEQ ID NO: 1.

3. The process according to claim 1, wherein at least 85% of the amount of intact phospholipids is reduced.

4. The process according to claim 1, wherein the polypeptide is capable of reducing at least 85% of the intact phospholipids originally present in the oil when the phospholipase A1 is incubated with the oil in an amount of 0.28 mg active protein/kg oil at a temperature of 55° C., 60° C., 65° C. and/or 70° C. for 4 hr.

5. The process according to claim 1, wherein the phospholipids comprise phosphatidic acid, phosphatidyl ethanolamine, phosphatidyl inositol, and/or phosphatidylcholine.

6. The process according to claim 1, further comprising adding an acid to the oil.

7. The process according to claim 1, further comprising adding water to the oil.

8. The process according to claim 1, further comprising adding a caustic to the oil.

9. The process according to claim 6, wherein the adding acid is performed before incubating the oil with the phospholipase.

10. The process according to claim 1, further comprising incubating the oil with a polypeptide having phospholipase C activity, a polypeptide having phosphatidylinositol phospholipase C activity and/or a polypeptide having phospholipase A2 activity.

11. The process according to claim 1, further comprising separating phosphorous-containing components from the oil.

12. The process according to claim 1, wherein the oil comprises a crude oil or water degummed oil.

13. The process according to claim 1, wherein the oil comprises a vegetable oil, algal oil, animal oil, or fish oil.

14. A triacylglyceride oil comprising a polypeptide having phospholipase A1 activity, wherein the polypeptide comprises a polypeptide having at least 80% identity to a mature amino acid sequence of SEQ ID NO: 1.

15. The oil according to claim 14, further comprising a polypeptide having phospholipase C activity, a polypeptide having phosphatidylinositol phospholipase C activity, and/or a polypeptide having phospholipase A2 activity.

16. The process according to claim 7 wherein the adding water is performed before incubating the oil with the phospholipase.

17. The process of claim 8, wherein the adding caustic is performed before incubating the oil with the phospholipase.

* * * * *

SEQUENCE LISTING

<160> NUMBER OF SEQ ID NOS: 4

<210> SEQ ID NO 1
<211> LENGTH: 298
<212> TYPE: PRT
<213> ORGANISM: Aspergillus niger
<220> FEATURE:
<221> NAME/KEY: MISC_FEATURE
<222> LOCATION: (1)..(298)
<223> OTHER INFORMATION: Amino acid sequence of phospholipase A1

<400> SEQUENCE: 1

```
Met Phe Leu Arg Arg Glu Phe Gly Ala Val Ala Ala Leu Ser Val Leu
1               5                   10                  15

Ala His Ala Ala Pro Ala Pro Ala Pro Met Gln Arg Arg Asp Ile Ser
                20                  25                  30

Ser Thr Val Leu Asp Asn Ile Asp Leu Phe Ala Gln Tyr Ser Ala Ala
            35                  40                  45

Ala Tyr Cys Ser Ser Asn Ile Glu Ser Thr Gly Thr Thr Leu Thr Cys
        50                  55                  60
```

Asp Val Gly Asn Cys Pro Leu Val Glu Ala Ala Gly Ala Thr Thr Ile
65                  70                  75                  80

Asp Glu Phe Asp Asp Ser Ser Ser Tyr Gly Asp Pro Thr Gly Phe Ile
                85                  90                  95

Ala Val Asp Pro Thr Asn Glu Leu Ile Val Leu Ser Phe Arg Gly Ser
            100                 105                 110

Ser Asp Leu Ser Asn Trp Ile Ala Asp Leu Asp Phe Gly Leu Thr Ser
            115                 120                 125

Val Ser Ser Ile Cys Asp Gly Cys Glu Met His Lys Gly Phe Tyr Glu
130                 135                 140

Ala Trp Glu Val Ile Ala Asp Thr Ile Thr Ser Lys Val Glu Ala Ala
145                 150                 155                 160

Val Ser Ser Tyr Pro Asp Tyr Thr Leu Val Phe Thr Gly His Ser Tyr
                165                 170                 175

Gly Ala Ala Leu Ala Ala Val Ala Ala Thr Val Leu Arg Asn Ala Gly
            180                 185                 190

Tyr Thr Leu Asp Leu Tyr Asn Phe Gly Gln Pro Arg Ile Gly Asn Leu
        195                 200                 205

Ala Leu Ala Asp Tyr Ile Thr Asp Gln Asn Met Gly Ser Asn Tyr Arg
    210                 215                 220

Val Thr His Thr Asp Asp Ile Val Pro Lys Leu Pro Pro Glu Leu Leu
225                 230                 235                 240

Gly Tyr His His Phe Ser Pro Glu Tyr Trp Ile Thr Ser Gly Asn Asp
                245                 250                 255

Val Thr Val Thr Thr Ser Asp Val Thr Glu Val Val Gly Val Asp Ser
            260                 265                 270

Thr Ala Gly Asn Asp Gly Thr Leu Leu Asp Ser Thr Thr Ala His Arg
        275                 280                 285

Trp Tyr Thr Ile Tyr Ile Ser Glu Cys Ser
    290                 295

<210> SEQ ID NO 2
<211> LENGTH: 897
<212> TYPE: DNA
<213> ORGANISM: Aspergillus niger
<220> FEATURE:
<221> NAME/KEY: misc_feature
<222> LOCATION: (1)..(897)
<223> OTHER INFORMATION: DNA sequence of phospholipase A1 (Genbank: XM_001393495)

<400> SEQUENCE: 2

```
atgtttctcc gcagggaatt tggggctgtt gcagccctat ctgtgctggc ccatgctgct      60
cccgcacctg ctccgatgca gcgtagagac atctcctcta ccgtcttgga caatatcgac     120
ctcttcgccc aatacagtgc agcagcttac tgctcctcca acatcgagtc caccggcacg     180
actctgacct gcgacgtagg caattgccct ctcgtcgagg cagccggtgc cacgaccatc     240
gatgagtttg acgacagcag cagctacggc gacccgacgg ggttcatcgc cgttgacccg     300
acgaacgagt taatcgttct gtctttccgg ggcagttccg acctctcgaa ctggattgcc     360
gacctagact tcggcctcac atccgtaagc agcatctgtg atggctgtga gatgcacaag     420
ggcttctacg aggcctggga agtcattgcc gacaccatca catccaaggt ggaggccgcc     480
gtctccagct atccggacta caccctcgtg ttcaccggac acagctacgg cgctgcattg     540
gcggctgtcg cggccaccgt gctccgcaac gccggataca ctcttgacct gtacaacttc     600
```

-continued

```
ggccagcccc gtattggcaa cctcgcctta gccgactaca tcaccgacca aaacatgggc    660
agcaactacc gcgtcacgca caccgatgac atcgtgccta agctgcctcc ggagctgctg    720
ggctaccacc acttcagtcc ggagtactgg atcaccagcg caatgatgt gacggtgaca    780 acgtcggacg tcaccgaggt cgtggggtg gattcgacgg ctgggaatga cggcacgctg    840
cttgacagta cgactgccca tcggtggtac acgatctaca ttagtgaatg ctcgtag     897
```

<210> SEQ ID NO 3
<211> LENGTH: 245
<212> TYPE: PRT
<213> ORGANISM: Artificial Sequence
<220> FEATURE:
<223> OTHER INFORMATION: Phospholipase C from WO2005/086900

<400> SEQUENCE: 3

```
Trp Ser Ala Glu Asp Lys His Asn Glu Gly Ile Asn Ser His Leu Trp
1               5                   10                  15

Ile Val Asn Arg Ala Ile Asp Ile Met Ser Arg Asn Thr Thr Ile Val
            20                  25                  30

Asn Pro Asn Glu Thr Ala Leu Leu Asn Glu Trp Arg Ala Asp Leu Glu
        35                  40                  45

Asn Gly Ile Tyr Ser Ala Asp Tyr Glu Asn Pro Tyr Asp Asp Ser
    50                  55                  60

Thr Tyr Ala Ser His Phe Tyr Asp Pro Asp Thr Gly Thr Thr Tyr Ile
65                  70                  75                  80

Pro Phe Ala Lys His Ala Lys Glu Thr Gly Ala Lys Tyr Phe Asn Leu
                85                  90                  95

Ala Gly Gln Ala Tyr Gln Asn Gln Asp Met Gln Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Met Gly Phe His Ser Lys
    130                 135                 140

Tyr Glu Asn Phe Val Asp Thr Ile Lys Asn Asn Tyr Ile Val Ser Asp
145                 150                 155                 160

Ser Asn Gly Tyr Trp Asn Trp Lys Gly Ala Asn Pro Glu Asp Trp Ile
                165                 170                 175

Glu Gly Ala Ala Val Ala Ala Lys Gln Asp Tyr Pro Gly Val Val Asn
            180                 185                 190

Asp Thr Thr Lys Asp Trp Phe Val Lys Ala Ala Val Ser Gln Glu Tyr
        195                 200                 205

Ala Asp Lys Trp Arg Ala Glu Val Thr Pro Val Thr Gly Lys Arg Leu
    210                 215                 220

Met Glu Ala Gln Arg Val Thr Ala Gly Tyr Ile His Leu Trp Phe Asp
225                 230                 235                 240

Thr Tyr Val Asn Arg
                245
```

<210> SEQ ID NO 4
<211> LENGTH: 298
<212> TYPE: PRT
<213> ORGANISM: Artificial Sequence
<220> FEATURE:
<223> OTHER INFORMATION: Phosphatidylinositol phospholipase C from
      WO2011/046812

<400> SEQUENCE: 4

-continued

```
Met Ala Ser Ser Ile Asn Val Leu Glu Asn Trp Ser Arg Trp Met Lys
1               5                   10                  15

Pro Ile Asn Asp Asp Ile Pro Leu Ala Arg Ile Ser Ile Pro Gly Thr
                20                  25                  30

His Asp Ser Gly Thr Phe Lys Leu Gln Asn Pro Ile Lys Gln Val Trp
            35                  40                  45

Gly Met Thr Gln Glu Tyr Asp Phe Arg Tyr Gln Met Asp His Gly Ala
        50                  55                  60

Arg Ile Phe Asp Ile Arg Gly Arg Leu Thr Asp Asp Asn Thr Ile Val
65                  70                  75                  80

Leu His His Gly Pro Leu Tyr Leu Tyr Val Thr Leu His Glu Phe Ile
                85                  90                  95

Asn Glu Ala Lys Gln Phe Leu Lys Asp Asn Pro Ser Glu Thr Ile Ile
                100                 105                 110

Met Ser Leu Lys Lys Glu Tyr Glu Asp Met Lys Gly Ala Glu Ser Ser
            115                 120                 125

Phe Ser Ser Thr Phe Glu Lys Asn Tyr Phe Arg Asp Pro Ile Phe Leu
        130                 135                 140

Lys Thr Glu Gly Asn Ile Lys Leu Gly Asp Ala Arg Gly Lys Ile Val
145                 150                 155                 160

Leu Leu Lys Arg Tyr Ser Gly Ser Asn Glu Ser Gly Gly Tyr Asn Phe
                165                 170                 175

Phe Tyr Trp Pro Asp Asn Glu Thr Phe Thr Ser Thr Ile Asn Gly Asn
            180                 185                 190

Val Asn Val Thr Val Gln Asp Lys Tyr Lys Val Ser Leu Asp Glu Lys
        195                 200                 205

Ile Asn Ala Ile Lys Asp Thr Leu Asn Glu Thr Ile Asn Asn Ser Glu
210                 215                 220

Asp Val Asn His Leu Tyr Ile Asn Phe Thr Ser Leu Ser Ser Gly Gly
225                 230                 235                 240

Thr Ala Trp Thr Ser Pro Tyr Tyr Tyr Ala Ser Arg Ile Asn Pro Glu
            245                 250                 255

Ile Ala Asn Tyr Ile Lys Gln Lys Asn Pro Thr Arg Val Gly Trp Ile
            260                 265                 270

Ile Gln Asp Phe Ile Asn Glu Lys Trp His Pro Leu Leu Tyr Gln Glu
        275                 280                 285

Val Ile Asn Ala Asn Lys Ser Leu Val Lys
290                 295
```